(12) United States Patent
Jones et al.

(10) Patent No.: US 7,294,102 B2
(45) Date of Patent: Nov. 13, 2007

(54) METHOD AND APPARATUS FOR PROVIDING DEPTH CONTROL OR Z-ACTUATION

(75) Inventors: Bradley Charles Jones, Endeavour Hills (AU); Christopher Gerard Byrne, Rowville (AU); Johan Gosse Lemmens, Ferntree Gully (AU); Libin Ni, Glen Waverley (AU)

(73) Assignees: PENTAX Corporation, Tokyo (JP); Optiscan PTY Ltd., Notting Hill (AU)

( * ) Notice: Subject to any disclaimer, the term of this patent is extended or adjusted under 35 U.S.C. 154(b) by 64 days.

(21) Appl. No.: 10/822,718

(22) Filed: Apr. 13, 2004

(65) Prior Publication Data

US 2004/0220453 A1    Nov. 4, 2004

Related U.S. Application Data

(60) Provisional application No. 60/462,324, filed on Apr. 14, 2003.

(51) Int. Cl.
*A61B 1/00* (2006.01)

(52) U.S. Cl. .............. 600/151; 600/160; 600/161; 600/163; 600/167; 600/168; 600/173; 385/117; 385/119

(58) Field of Classification Search .............. 600/151, 600/160, 167–168, 173, 182; 385/117, 119; 359/823, 826
See application file for complete search history.

(56) References Cited

U.S. PATENT DOCUMENTS

| | | | | |
|---|---|---|---|---|
| 4,540,937 A * | 9/1985 | Asars | ........................... | 324/96 |
| 4,884,557 A * | 12/1989 | Takehana et al. | ........... | 600/145 |
| 4,930,494 A * | 6/1990 | Takehana et al. | ........... | 600/145 |
| 5,191,879 A * | 3/1993 | Krauter | ...................... | 600/109 |
| 5,531,664 A * | 7/1996 | Adachi et al. | ................. | 600/149 |
| 6,217,510 B1 * | 4/2001 | Ozawa et al. | ................ | 600/129 |
| 6,641,530 B2 * | 11/2003 | Mitsumori | .................. | 600/167 |

FOREIGN PATENT DOCUMENTS

WO        00/75712        12/2000

\* cited by examiner

*Primary Examiner*—Linda C. M. Dvorak
*Assistant Examiner*—Matthew J. Kasztejna
(74) *Attorney, Agent, or Firm*—Greenblum & Bernstein, P.L.C.

(57) ABSTRACT

A position control apparatus for controlling position along an axis, comprising: an extensible member that can be extended and contracted along said axis, comprising shape memory alloy locatable to expand and contract along said axis, heating means for controlling said temperature of said shape memory alloy, and a feedback mechanism for controlling said heating means and responsive to variations in said position, wherein said position is controllable by means of said heating means and can be stabilized by means of said feedback mechanism.

44 Claims, 9 Drawing Sheets

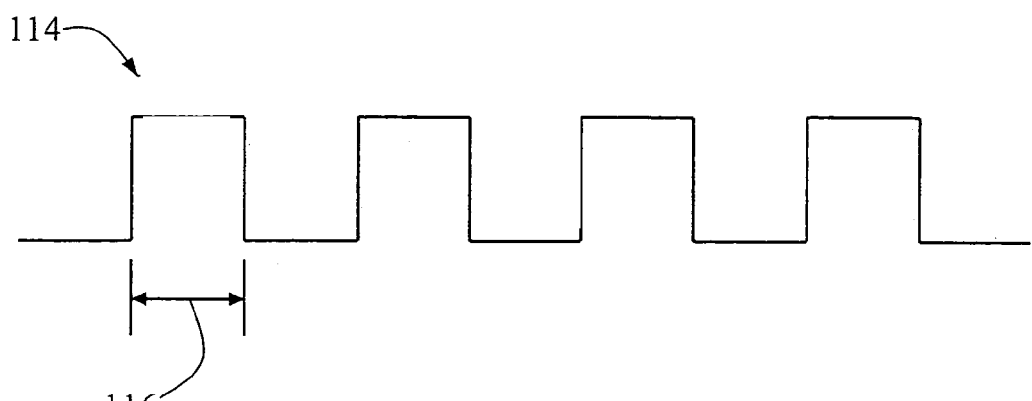
Figure 5A
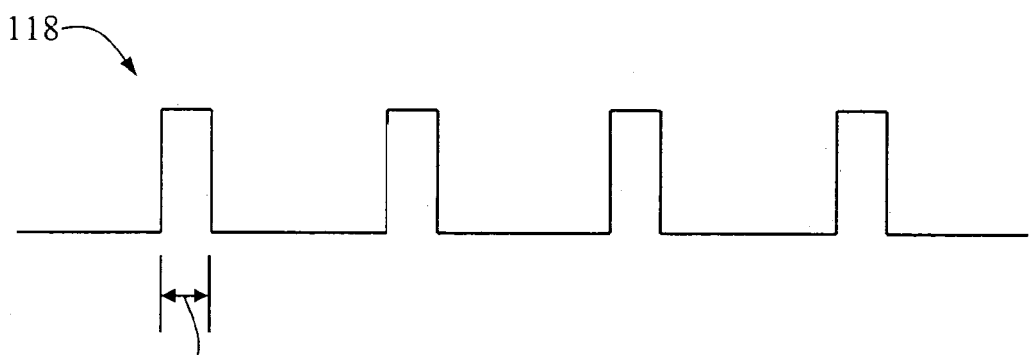
Figure 5B
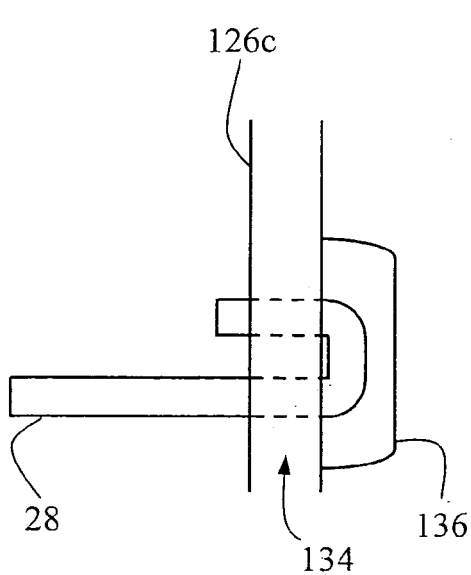 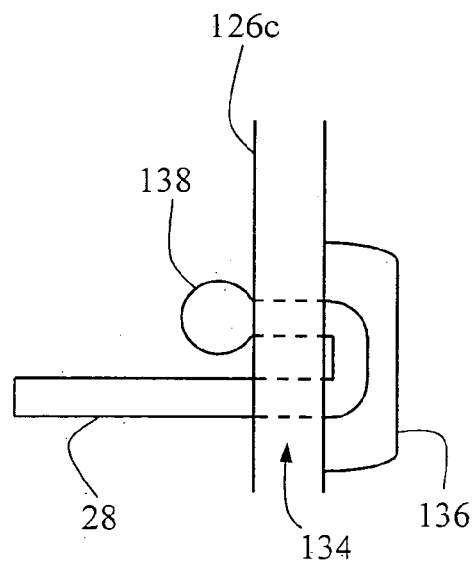
Figure 7A                Figure 7B

METHOD AND APPARATUS FOR PROVIDING DEPTH CONTROL OR Z-ACTUATION

This application is based on and claims the benefit of the filing date of U.S. provisional application Ser. No. 60/462,324 filed 14 Apr. 2003 and incorporated herein by reference in its entirety.

FIELD OF THE INVENTION

The present invention relates to a method and apparatus for providing depth control or z-axis actuation in, for example, optical instrumentation such as endoscopes and microscopes (including endomicroscopes).

BACKGROUND OF THE INVENTION

Many techniques have been proposed for providing x-y actuation, that is, scanning: see, for example, WO 00/75712. Actuation in the z or depth direction is also often required, particularly in endoscopy and microscopy and, in particular, in confocal systems. In one existing approach, z depth adjustment is provided by manual adjustment of the position of an objective lens. In bench-top systems this may be done by direct adjustment; in hand held devices this is done, in one existing system, by means of a mechanical cam system operated by the user. In confocal microscopy systems, a z depth adjustment mechanism is required to enable the operator to focus the confocal point within a specimen at different focal plane depths.

However, existing z-actuator systems are inappropriate for miniaturized confocal endoscopes and other compact systems where dimensions (and, in particular, diameter) are required to be minimized, or where, as in endoscopy, the length of the rigid head should be as short as possible.

It is an object of the present invention to provide a z actuator that is controllable in the z axis but provides some flexibility in lateral directions.

SUMMARY OF THE INVENTION

The present invention provides, in a first broad aspect, a position control apparatus for controlling position along an axis, comprising:
  an extensible member that can be extended and contracted along said axis, comprising shape memory alloy locatable to expand and contract along said axis;
  heating means for controlling the temperature of said shape memory alloy; and
  a feedback mechanism for controlling said heating means and responsive to variations in said position;
  wherein said position is controllable by means of said heating means and can be stabilized by means of said feedback mechanism.

In one embodiment, the axis is the depth or z axis (in which case the apparatus may be described as a depth control or z-actuation apparatus).

Preferably the apparatus includes biasing means for opposing either the expansion or contraction of said shape memory alloy, preferably opposed to said contraction.

Preferably the biasing means is a spring and more preferably a coil spring, but it could also comprise a member of rubber or some other resilient material that is, for example, compressed when the when the shape memory alloy contracts.

Thus, fluctuations in the length of the shape memory alloy arising from variations in ambient temperature are corrected by means of the feedback mechanism so that the apparatus maintains a desired length once set to that length. Examples of suitable shape memory alloys are tinel and nitinol.

Preferably the feedback mechanism comprises a feedback sensor for sensing the position of the apparatus and provide an output directed to the heating means to modify the heat applied to the shape memory alloy.

In one embodiment, the feedback mechanism comprises a plurality of feedback sensors. By this means, a more accurate measure of position can be obtained or, where the distance being measured is not uniform (such as if the apparatus is being bent), a measure of the degree of bend so that the appropriate position value can be determined.

Preferably the heating means comprises a source of electrical current for heating said shape memory alloy, preferably by passing said electrical current through said shape memory alloy. However, the heating means could be any other suitable alternative, including a mechanism for heating and circulating a fluid (including air, another gas or a liquid) around or past the shape memory alloy. Alternatively, the heating means could comprise a heater touching or otherwise in thermal communication with the shape memory alloy (such as one or more electrically powered heating elements operable to radiate heat onto the shape memory alloy, or connected to the shape memory alloy by a thermally conductive connector).

Preferably said electrical current is a pulse width modulated current. Preferably, the heating means is controllable to vary the duty cycle of the pulse width modulated current and therefore the average value of the electrical current.

Thus, by changing the average value of the current, the heating of and therefore the length of the shape memory alloy can be controlled.

The feedback mechanism may comprise a capacitance sensor, a variable resistance sensor, a magnetic hall sensor, an inductive sensor, or an optical sensor. In one embodiment the feedback mechanism comprises a capacitive sensor comprising a double wire coil capacitive sensor, wherein the separation of the two coils varies according to the position of said apparatus thereby varying the output of said sensor. In a preferred embodiment the feedback mechanism comprises an optical sensor comprising a pulsed red Light Emitting Diode (LED) and a Phase Locked Amplifying (PIN) detecting diode.

Preferably said apparatus includes an elongate member for securing said shape memory alloy to said apparatus, wherein said elongate member is longitudinally substantially rigid and laterally flexible. More preferably said elongate member comprises a Bowden Cable.

The present invention also provides an endoscope comprising:
  an optical fibre for providing illuminating light;
  a light condenser for focussing said illuminating light to an observational field; and
  a position control apparatus as described above, for controlling the position of the observational field.

The position may be adjustable by movement of the exit aperture, by movement of the light condenser, or by movement of both the exit aperture and the light condenser, wherein the movement is controllable by means of the position control apparatus.

Preferably said endoscope includes an x-y scan mechanism incorporating said exit aperture, wherein said x-y scan mechanism is adjustable in position by means of said position control-apparatus.

In one embodiment the extensible member is one of a plurality of like extensible members.

Thus, a plurality of such members of shape memory alloy could be included. This might be to reduce the range of heating required in each, or to allow more evenly distributed force to be applied to effect changes in z position. Alternatively, different heating applied to respective members can be used to bend a device in which the apparatus is employed. For example, where the apparatus is used to control the z position of an x-y scan mechanism, the x-y scan mechanism could be induced to adopt an orientation at an angle to the apparatus by locating, for example, three separately controlled members evenly spaced around the circumference of the apparatus.

The endoscope, in one embodiment, is a confocal endoscope, and may be in the form of an endomicroscope.

The present invention also provides a microscope (which may be a confocal microscope) comprising:
 a position control apparatus as described above, for controlling the position of an observational field of said microscope.

The present invention also provides a colonoscope (which, also, may be confocal) having a position control apparatus as described above.

In one embodiment, the apparatus includes a flexible printed circuit board (PCB) arranged between and attached to two portions of said apparatus whose separation varies as the position is varied, to flex as said separation varies.

This approach could in fact be used in other applications where the separation of two components varies, and an electrical connection is required or desired between those two portions.

Preferably said apparatus includes a home adjustment mechanism for setting a desired home position in the direction of the axis (such as a z direction), such that subsequent adjustment of the position is relative to said home position.

The present invention also provides, in a second broad aspect, a method of providing positioning control of a position along an axis, comprising:
 providing a extensible member that can be extended and contracted along said axis, comprising shape memory alloy locatable to expand and contract along said axis;
 controlling the length of said shape memory alloy by means of heating means; and
 providing a feedback signal in response to variations in said position and controlling said heating means according to said feedback signal to stabilize said position;
 whereby said position is controllable by means of said heating means and stabilized by means of said feedback mechanism.

The axis may be is the depth or z axis.

Preferably the method includes opposing either the expansion or contraction of said shape memory alloy by means of a biasing means, such as a spring, preferably opposed to said contraction.

The invention also provides a method of performing endoscopy or colonoscopy of a site, comprising:
 locating an optical head at said site; and
 controlling the position of an observational field of said endoscopy or colonoscopy at least in part by means of a shape memory alloy.

BRIEF DESCRIPTION OF THE DRAWINGS

In order that the invention may be more clearly ascertained, preferred embodiments will now be described, by way of example, with reference to the accompanying drawings, in which:

FIG. 5A is a schematic representation of the square wave voltage input to the driver of the z control apparatus of FIG. 1A;

FIG. 5B is a schematic representation of the square wave voltage input to the driver of the z control, apparatus of FIG. 1A following depth adjustment;

FIG. 7A is a schematic view of the attachment of the nitinol wire and-the forward PCB of the z control apparatus of FIG. 1A; and FIG. 7B is a schematic view of an alternative form of attachment between the nitinol wire and the forward PCB of the z control apparatus of FIG. 1A.

DETAILED DESCRIPTION OF THE DRAWINGS

FIG. 1 is a schematic diagram of a colonoscope insert 10 provided with a z control apparatus for controlling the focal plane of the colonoscope insert 10 in the depth or z direction 12 according to a preferred embodiment of the present invention. The colonoscope insert 10 constitutes that portion of a colonoscope that, in use, would be inserted into a colon; this figure omits, therefore, the colonoscope's hand-piece, controls, etc.

Figure 1A:
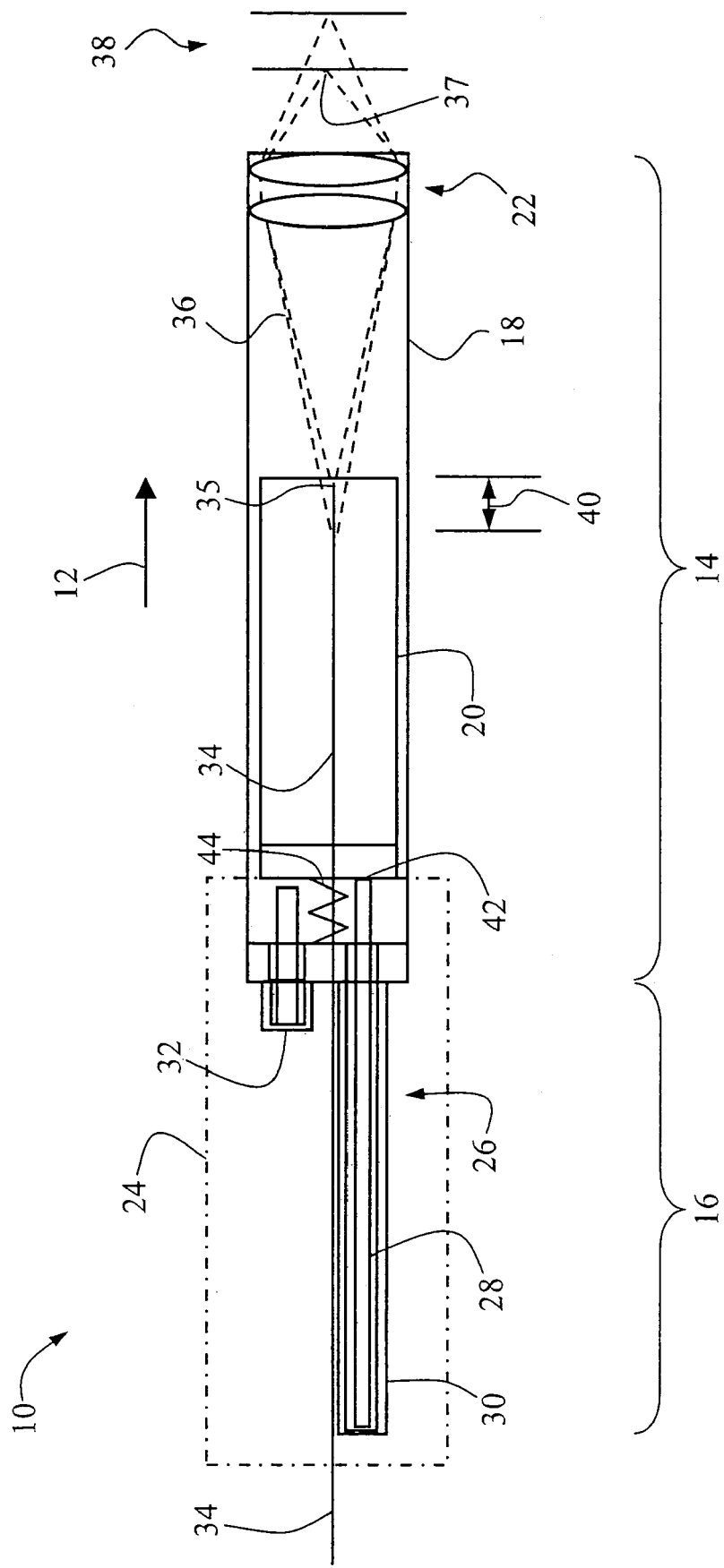
FIG. 1A is a schematic view of a colonoscope insert provided with a z control apparatus for controlling the focal plane of the colonoscope in the depth or z direction according to a preferred embodiment of the present invention.
Figure 1B:
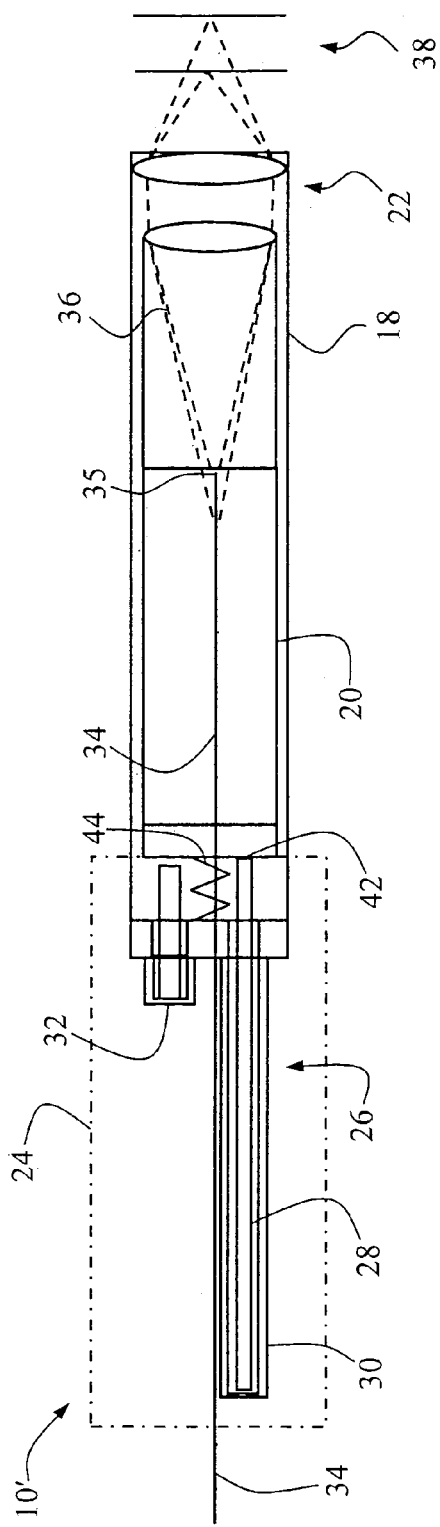
FIG. 1B is a schematic view of a colonoscope insert provided with a z control apparatus for controlling the focal plane of the colonoscope in the depth or z direction according to an alternative preferred embodiment of the present invention.
Figure 1C:
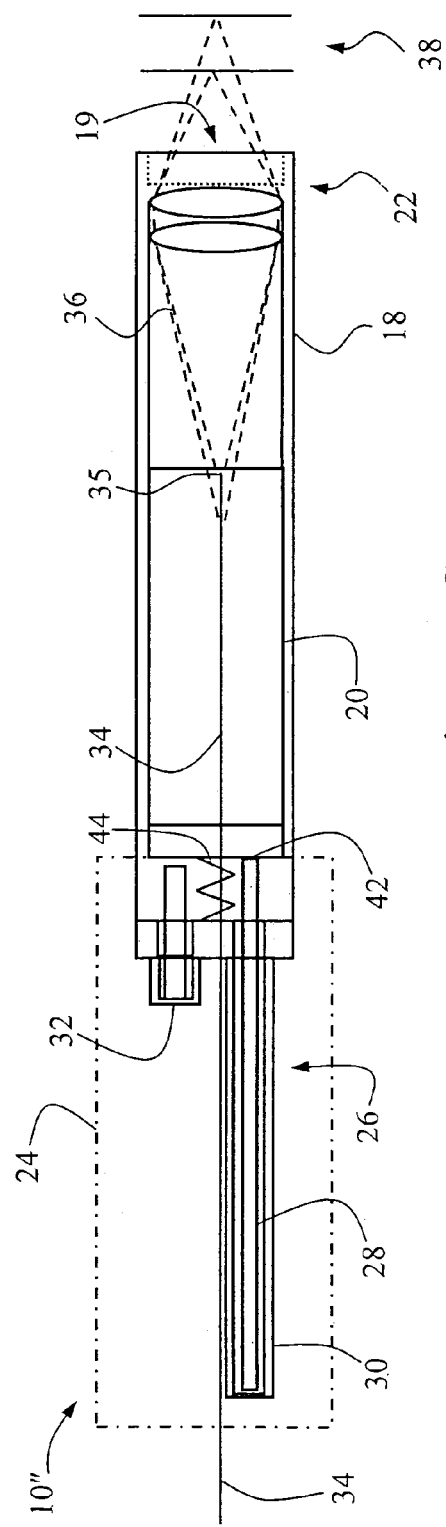
FIG. 1C is a schematic view of a colonoscope insert provided with a z control apparatus for controlling the focal plane of the colonoscope in the depth or z direction according to a still further preferred embodiment of the present invention.

The colonoscope insert 10 includes a relatively rigid forward section 14 and a relatively flexible rear section 16. The forward section 14 principally comprises an external tubular housing 18 with an x-y scan mechanism 20 and an objective optics train 22. In FIG. 1A, the optics train 22 is shown schematically as comprising two representative lenses. It will be understood, however, that the optics train 22 could comprise a single lens, but will usually comprise a complex lens that may include a plurality of optical elements, each comprising a convex lens, a concave lens or a planar element.

The rear section 16 contains the principal components of a z control apparatus 24, viz. a z actuator 26 comprising a rearwardly extending wire 28 of the shape memory alloy nitinol, an elongate member in the form of a Bowden Cable 30 (attached at one end to the rearward end of the nitinol wire 28 and at the other end to the rear end of the housing 18), and a position sensor 32.

An optical fibre 34, which transmits both illuminating (typically laser) light 36 to a point observational field 37 on or within the colon and return light for detection after emanation (as reflected, or fluoresced light) from that point observational field, is located on the central, longitudinal axis of the colonoscope insert 10 though extends only as far forward as the forward end of the x-y scan mechanism 20. A laser source and detector (not shown) are ultimately coupled to this fibre 34 via a beam-splitter (also not shown) to separate the illuminating and emanating light. The optics train 22 includes lenses for focussing the illuminating light from the exit aperture of the exit tip of the fibre 34 to the point observational field 37, and to collect and focus return light back into the fibre 34.

The colonoscope insert 10 operates confocally, the exit aperture of the fibre 34 acting as a spatial filter so that the depth of field of the colonoscope is constrained to a well-defined focal plane 38 either on or below the surface of the tissue being examined. However, the x-y scan mechanism 20 is slidable in reciprocating fashion within the housing 18 along the z direction, that is, towards or away from the forward end of the external housing 18. In this embodiment, the optics train 22 is, in normal operation, fixed relative to the external housing 18; consequently, the x-y scanning mechanism 20 is slidable towards or away from the objective optics train 22 so that the location of the focal plane 38 is varied. In another embodiment, however, the x-y scan mechanism 20 is slidable in association with a selected rearward subset of the optical elements constituting the optics train 22 so that the remaining optical element or elements remains or remain fixed relative to the external housing 18. On one example of this embodiment, only the forward-most optical element is left stationary while the other elements are moved. This embodiment is shown schematically at 10' in FIG. 1B, in which each illustrated lens is purely representative of one or more optical elements (as discussed above).

In a further embodiment, the x-y scan mechanism is slidable in association with all of the optical elements in the objective optics train 22 that a tubular space of variable z dimension is created at the end of the housing 18 between the last (i.e. most forward) optical element and the specimen. The specimen may then partially protrude into this tubular space thereby enhancing tissue stability and ease of imaging. This embodiment including the tubular space 19 is shown schematically at 10" in FIG. 1C, in which each illustrated lens is also representative of one or more optical elements (as discussed above).

Thus, in each of these embodiments the examined field of view can thereby be controlled to a degree (over the range 40 in the z direction of about 300 μm) without making coarse adjustments to the position of the colonoscope insert 10. The z control apparatus 24 is provided to effect this sliding and hence repositioning of both the x-y scan mechanism 20 and the focal plane 38 relative to the colonoscope insert 10 and the sample being viewed.

The actual range of positions accessible by moving focal plane 38 is from just rearward of the forward-most optical element of optics train 22 to approximately 300 μm forward of that last optical element.

It should be noted that the optical fiber 34 is securely attached to the x-y scan mechanism 20, as the exit tip 35 of the fiber 34 is moved in x and y directions by the scan mechanism 20. This also ensures that, when the x-y scan mechanism 20 is advanced or retracted by the z control apparatus 24, so too is the exit tip 35 of fiber 34 thereby correspondingly advancing or retracting the focal plane 38 in the z direction. In moving the x-y scan mechanism 20 and exit tip 35 over a range of 300 μm, the fiber 34 will be placed under tension or expansion in the region rearward of the x-y scan mechanism. However, in this region (which includes the region of over 1 m outside the endoscope head) the fiber 34 is encased in a sleeve (not shown) within which it can move sufficiently to allow for this effect. It will be appreciated that such movement is, in any event, normal, as it will also occur when the colonoscope is manipulated into place for colonic examination.

Broadly speaking, to achieve forward and rearward z actuation, the forward end 42 of the nitinol wire 28 is attached to the rear of the x-y scan mechanism 20. Heating the nitinol wire 28 causes it to contract and therefore drag the x-y scan mechanism 20 rearward; allowing the nitinol wire 28 to cool enables it to expand and, assisted by a coil spring 44 located between the housing 18 and the rear of the x-y scan mechanism 20, slide the x-y scan mechanism 20 forward. The spring 44 is represented schematically in this figure but is described, together-with components adjacent to the spring 44, in greater detail below.

As explained above, the focal plane 38 of the colonoscope insert 10 moves with this movement of x-y scan mechanism 20 in the z direction 12. Any of several techniques would be suitable for attaching the nitinol wire to the Bowden Cable 30 or to the rear of the x-y scan mechanism 20. The wire 28 can be attached by means of crimping, or alternatively the end sections of the nitinol wire 28 can be expanded and slotted into notched sections of the adjoining materials (i.e. the Bowden Cable 30 or to the rear of the x-y scan mechanism 20). Another approach is to thread the nitinol wire 28 through pre-drilled holes in the adjoining materials, and then loop the wire over or orient it at a different angle to the tensional force being applied to the attachment point. In this approach, additional crimping may be also employed, to obtain a more secure attachment.

Fluctuations in temperature within the z control apparatus 24, however, will cause the nitinol wire 28 to vary in length even when its temperature is notionally being held constant. Unchecked, this will produce unwanted fluctuations in the position of focal plane 38. The action of the z control apparatus 24 is therefore stabilized by means of a feedback mechanism comprising principally the position sensor 32. The position sensor 32 detects the position of the x-y scan mechanism 20 relative to the position of the housing 18 and provides a varying output signal that, as a consequence, is a measure of the position of the focal plane 38. This signal can then be used to correct any undesired fluctuation on the length of the nitinol wire 28 and hence wander in the position of the focal plane 38. The desired stability of the position of the focal plane 38, once set, is of the order of 10 μm. Further, this feedback minimizes the magnitude of any drift in this position due to the bending of the colonoscope (in its flexible section 16 or between that section and its hand-piece (not shown)).

The feedback mechanism also has as short as possible a response time from between when an operator sets a new z depth or position and attaining that position. This response time includes the response time of the circuitry (see FIGS. 3A and 3B) and of the nitinol wire 28 itself once a necessary heating current begins passing through, it. The former is desirably between 5 and 100 ms. When contracting the wire 28 by heating, the latter depends on the rate of temperature change within the nitinol wire 28 and the mechanical resistance of the x-y scan mechanism 20 (including against spring 44). When expanding the wire 28 by reducing heating, the latter depends on the rate of heat dissipation from the wire 28 and the action of the wire 28 against the spring 44. It has been found that the present embodiment can be adjusted from one extreme z depth to the other in 10 s.

Importantly, the heating current through the wire 28 should be minimized to keep operating temperatures to a minimum, both for patient safety and so that the heat that must be dissipated when cooling the wire 28 is minimized.

Figure 2A:
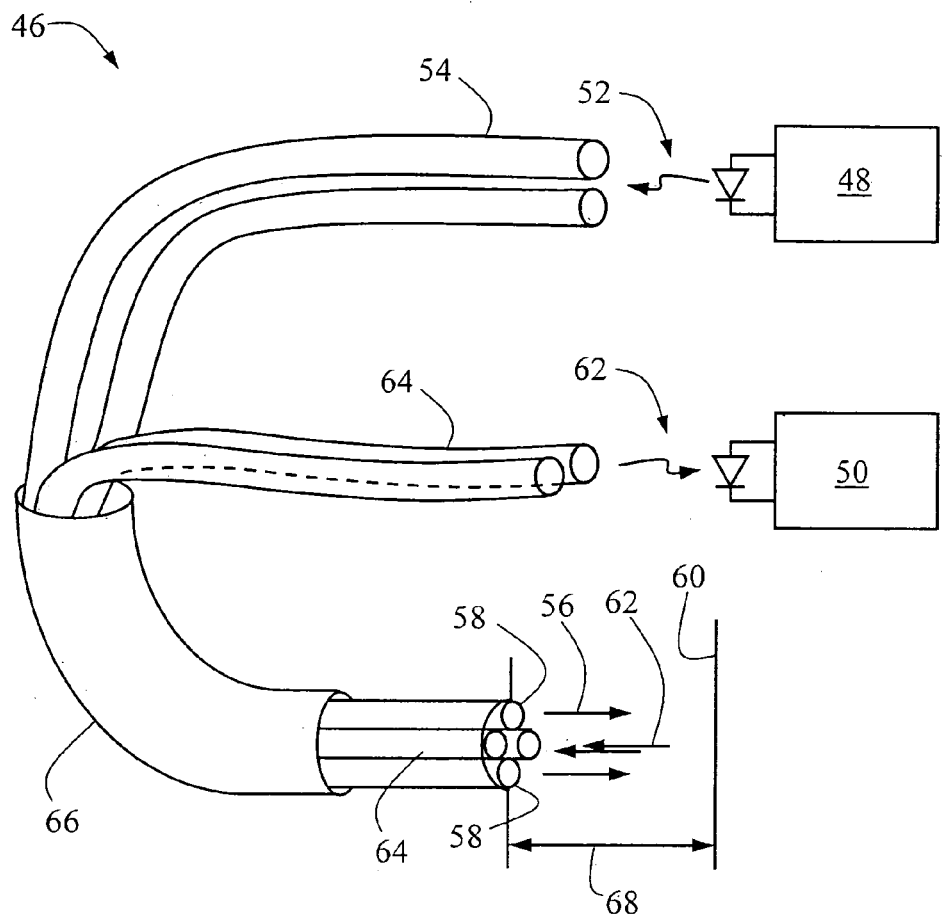
FIG. 2A is a schematic view of the optical position sensor of the z control apparatus of FIG. 1A.

The position sensor 32 of this embodiment comprises an optical intensity sensor, shown generally at 46 in FIG. 2A. The optical position sensor 46 comprises a pulsed red Light Emitting Diode (LED) 48 and a Phase Locked Amplifying (PIN) detecting diode 50. The pulsed light 52 emitted from the LED 48 is focused into a pair of optical fibres 54 by means of a focussing lens (not shown). This light is emitted 56 from the projecting remote ends 58 of the pair of optical fibres 54, and is directed onto the rear surface 60 of the x-y scan mechanism 20. Light reflected 62 from the rear surface 60 is then collected by a second pair of optical fibres 64. The first and second pairs of fibres 54,64 together form an optical fibre bundle 66. The second pair of fibres 64 transmit the reflected light 62 to the detecting diode 50. The first and second pairs of optical fibres 54,64 are arranged in a cross-matched configuration within the bundle 66 such that the first pair are in a plane at right angles to the plane defined by the second pair, in order to maximize measurement accuracy.

The intensity of the light detected by the diode 50 in the optical position sensor 46 varies in relation to the distance 68 between the surface 60 and the end of the optical fibre bundle 66; this distance 68 varies with the position of the x-y scan mechanism 20, and is therefore indicative of the length of the nitinol wire 28. Movement of the x-y scan mechanism 20 in the housing 18 thus detected by the detecting diode 50, which converts the mechanical displacement (by means of a converter, not shown) into an analogue voltage signal, O (V), that is therefore indicative of that mechanical displacement.

Figure 2C:
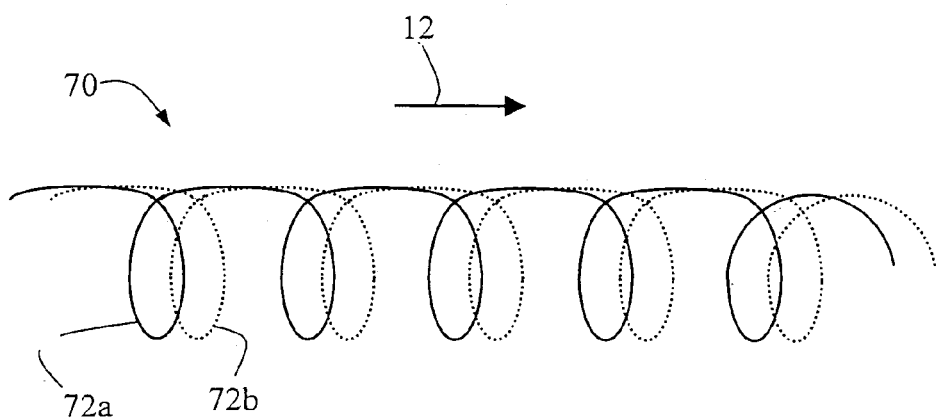
FIG. 2C is a schematic view of a capacitance position sensor according to an alternative preferred embodiment of the z control apparatus of FIG. 1A.
Figure 2B:
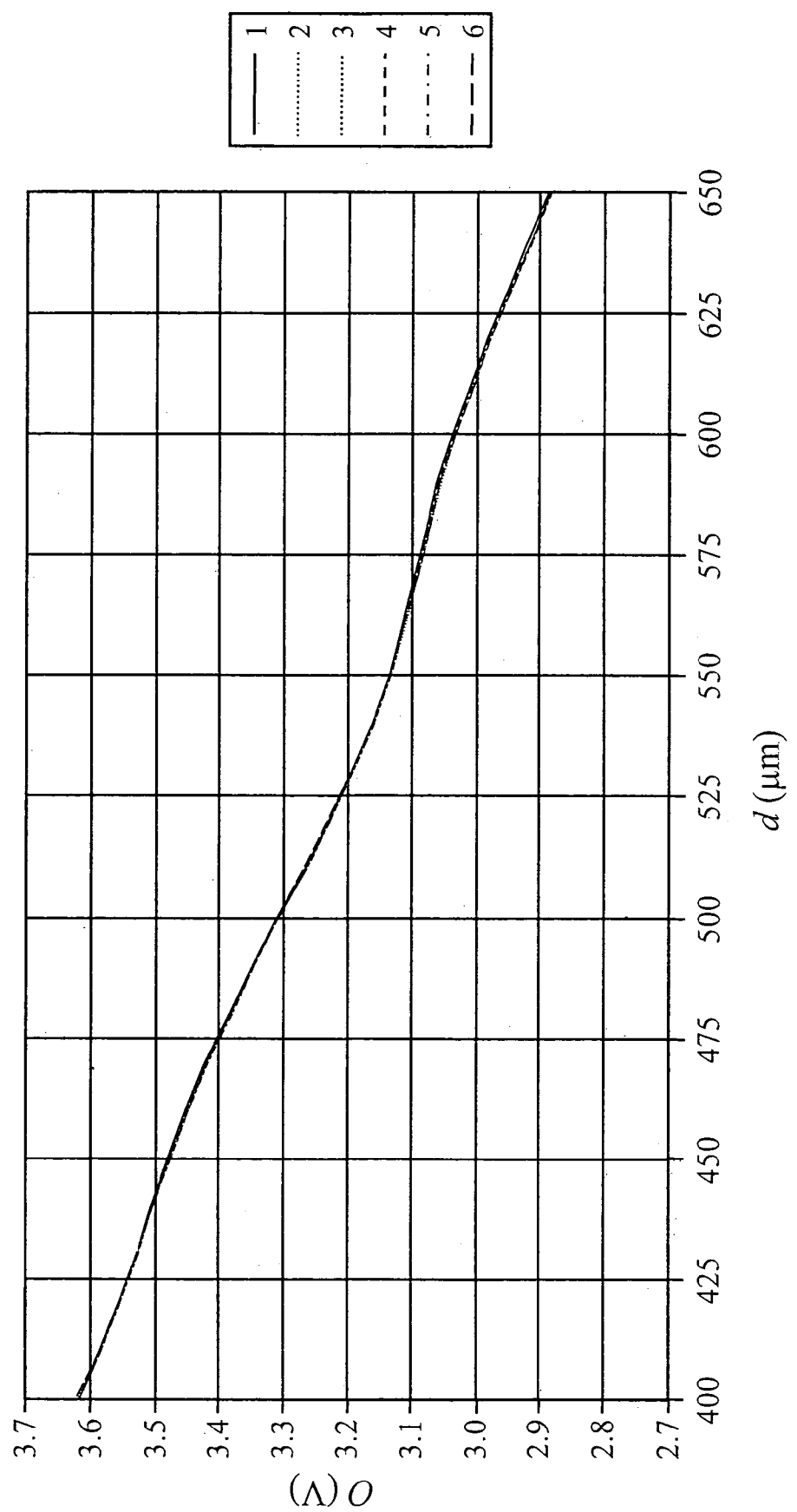
FIG. 2B is the measured relationship between the change in output analogue volts with the change in the distance of the z actuation for the optical position sensor of FIG. 2A.

The relationship between analogue voltage signal and the mechanical displacement has been measured in a series of six tests, and is plotted in FIG. 2B as a function of displacement d ($\mu$m). The curve corresponding to each test is labelled with the number of the test in a key to the right of the graph. Over the range of 400 to 650 $\mu$m in mechanical displacement, the analogue voltage signal follows an approximately linear relationship, a relationship closely replicated in the six tests.

It is possible to use different types of position sensor to provide the desired feedback as long as the physical size meets the physical constraints of the colonoscope insert 10.

Thus, referring to FIG. 2C, the position sensor 32 may alternatively comprise a double wire coil capacitive sensor 70, in which the coils 72a, 72b of the sensor 70 vary in separation according to the length of the sensor 70. The two coils 72a, 72b are not joined in a circuit and thus have a capacitance that increases as the two coils 72a, 72b are drawn closer together (upon contraction of the sensor 70). The sensor 70 is aligned in the z direction 12, so variations in the position of the x-y scan mechanism 20 (relative to the housing 18) result in such variations in the separation-of the coils 72a, 72b. This occurs when the nitinol wire 28 contracts and draws the x-y scan mechanism 20 rearward, compressing the sensor 70, or expands allowing the x-y scan mechanism 20 to be urged forward by the spring 44, extending the sensor 70. Hence the closer relative to the position of the housing 18 as set by the z control apparatus 24. Movement of the x-y scan mechanism 20 in the housing 18 is hence detected by the capacitive position sensor 70, which converts the mechanical displacement (by means of a converter, not shown) into an analogue voltage signal that is therefore indicative of that mechanical displacement.

The capacitive position sensor 70 thus provides the capacitive change with the movement of the x-y scan mechanism 20.

Figure 3A:
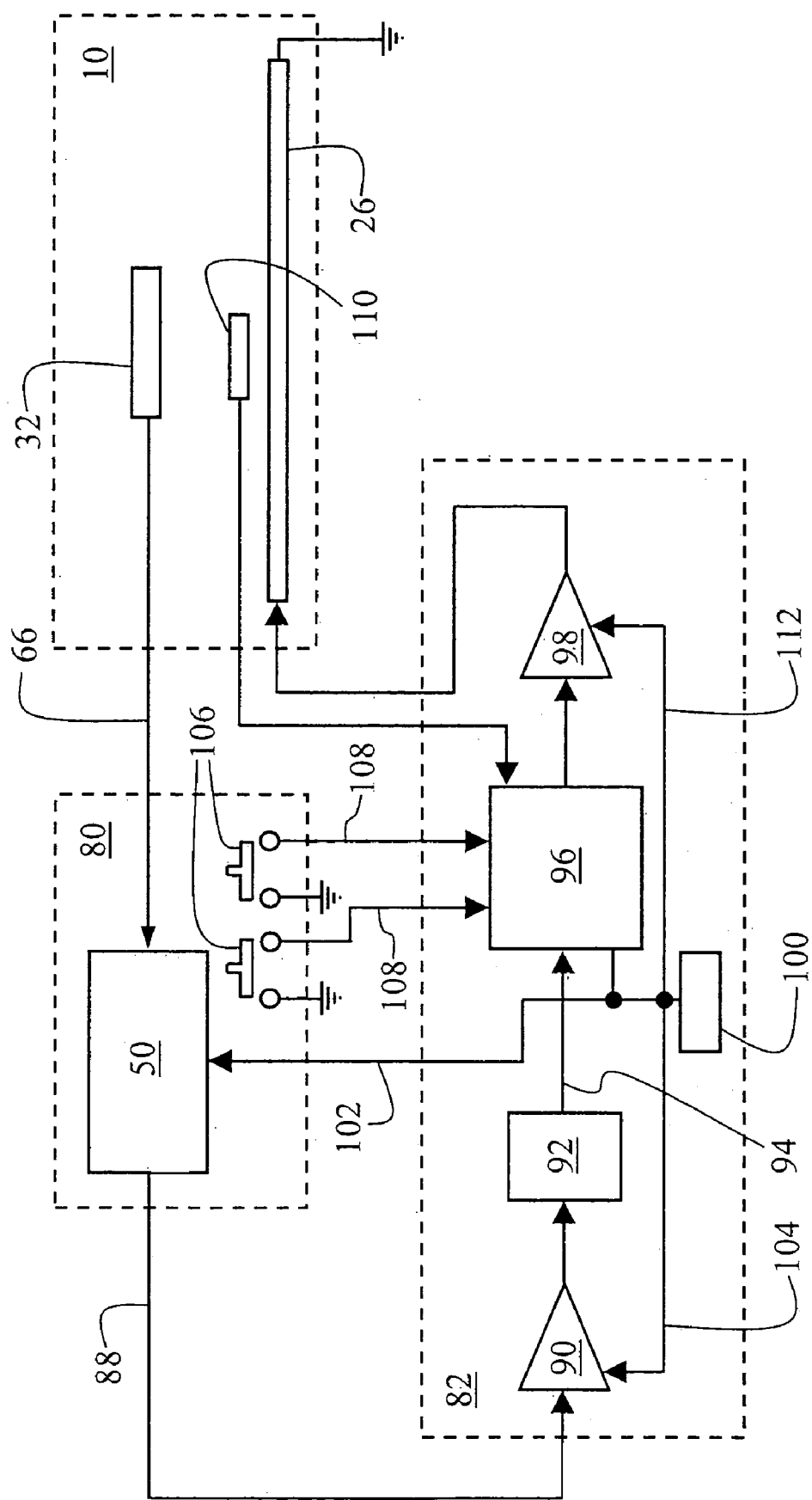
FIG. 3A is a schematic circuit diagram of the colonoscope with z control apparatus with optical position sensor of FIG. 1A.

FIG. 3A is a schematic circuit diagram of the colonoscope whose insert 10 and z control apparatus 24 are shown in FIG. 1. As mentioned above, the colonoscope insert 10 is one component of the colonoscope, which also includes a hand-piece 80 and a controller board 82. Each of these three components (insert 10, hand-piece 80 and controller board 82) has its own direct independent power supply (not shown in FIG. 3A).

The hand-piece 80 includes detecting diode 50, which picks up the change of signal from the position sensor 32, as discussed above, and converts it into an analogy voltage signal 88 that is indicative of the mechanical displacement of the x-y scan mechanism 20. The detecting diode 50 directly outputs an analogue voltage signal in response to varying light intensities detected. The change range of output voltage 88 is greater than 600 mV.

Although in this embodiment the detecting diode 50 is located in the hand-piece 80, this diode and LED 48 could be located essentially anywhere within the system. This is because the length of the cross-matched configuration of pairs of optical fibre 54,64 is not critical to the accuracy of the optical position sensor 32. For example, the LED 48 and the detecting diode 50 could be sufficiently small to be placed directly on the surface of one of the PCBs within the colonoscope insert 10 and in this embodiment the cross-matched pairs of optical fibre 54,64 would not be needed. Instead, light emitted by LED 48 could be reflected directly from the rear surface 60 of the x-y scan mechanism 20 and then detected by the detecting diode 50.

Figure 3B:
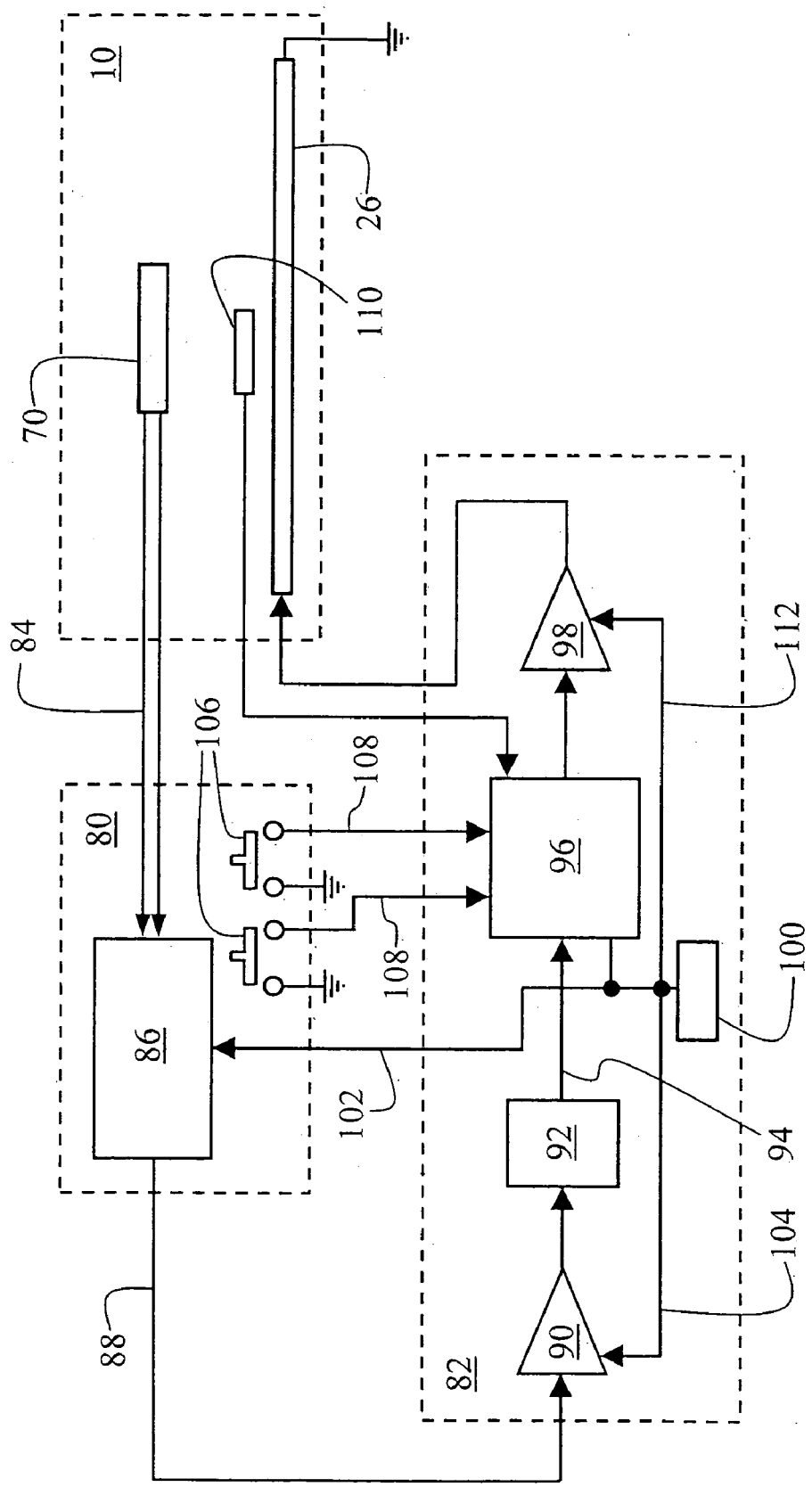
FIG. 3B is a schematic circuit diagram of a colonoscope with z control apparatus with capacitive position sensor according to an alternative preferred embodiment of the present invention.

Referring to FIG. 3B, in the alternative embodiment where the position sensor 32 comprises the double wire coil capacitance sensor 70, the hand-piece 80 includes a converter 86 comprising a demodulator with its own excitation and demodulation circuits (instead of detecting diode 50).

It would be advantageous to locate the converter 86 as near as possible to the capacitance position sensor 32, as any additional lengths of electrical cable from the capacitance position sensor 32 to the converter 86 adds additional capacitance; measured changes in the capacitance of the sensor 32 thereby become lower in percentage terms.

In one test, the capacitance of the capacitive position sensor 32 was measured and found to be 110 pf when fully extended and 140 pf when compressed, a capacitance range (i.e. 140–110=30 pf) of 24% of the mean (i.e. (140+110/2) =125 pf). A percentage range of this order should therefore be obtained if the converter 86 is placed adjacent to the sensor 32. A change of capacitance of the order of 24% should be easily detected above background noise and easily inputted into the feedback loop through output 88.

However, in the embodiment shown in FIG. 3B, space constraints in the colonoscope insert 10 mean that the converter 86 is not readily located within the insert 10. The next closest convenient position for the converter 86 is in the hand-piece 80, which is therefore its position as shown in FIG. 3B.

A length of approximately 2 m of low capacitance electrical cable 84 is used between the capacitive position sensor 70 and the converter 86. This low capacitance cable has a measured capacitance of 130 pf/m. Accordingly, the percentage change in capacitance being measured by the converter 86 when located in the hand-piece 80 is in fact $30/(125+2\times130) = \sim 8\%$.

If instead the converter 86 were positioned within the controller board 82 then an even greater length of cable would be required between the converter 86 and the position sensor 32. A lower percentage change in capacitance as detected by the converter 86 effectively means that either the accuracy of the positional feedback mechanism and/or its speed of iteration would be compromised at least to some extent.

The converter 86 drives an AC half-bridge by means of an AC signal, in which one arm comprises a fixed capacitor. (The other arm, in this embodiment, effectively comprises the two coils 72a, 72b of the capacitive position sensor 70.) The mechanical displacement of the x-y scan mechanism 20 causes changes in the amplitude of AC signal in the position sensor 32 (owing to an impedance change). The converter 86 compares the signal from position sensor 32 with the excitation signal and demodulates the difference between them into a DC voltage. The change range of output voltage 88 from the converter 86 is greater than 200 mV. The zero offset voltage of the converter 86 is adjustable to fit each particular position sensor 32.

Thus, as explained above the signal from the detecting diode 50 (cf. FIG. 3A) or from the converter 86 (cf. FIG. 3B) is output as an analogue voltage signal 88; this signal is transmitted to the controller board 82 where it is scaled firstly by an amplifier 90 and then converted by an Analogue to Digital Converter (ADC) 92 into a digital signal 94 of data for further processing.

The amplifier 90 comprises a low noise operational amplifier, a low pass filter and a digital potentiometer. The input signal, as it comes from the converter 86, has a maximum amplitude (span) of typically 200 mV; typically the maximum amplitude of the output is set to between 1 and 4 V.

The micro-controller 96 on controller board 82 collects the digital signal from the ADC 92 and computes the necessary signals to control a driver 98 (also on controller board 82) to drive the z actuator 26, as is described in greater detail below. In broad terms, the driver 98 directs a pulse width modulated current through the wire 28 to heat and thereby vary the length of the wire 28. The heating is controlled by varying the duty cycle of the modulated current and hence the average value of the current and therefore the heating effect on the wire 28.

The ADC 92 is a 12 bit, serial analogue to digital converter that converts the analogue signal from the amplifier 90 into a digital signal 94. It interfaces with and is controlled by the micro-controller 96 while in turn receiving transformed signals ultimately from the position sensor 32.

The gain of the amplifier 90 can be adjusted by the micro-controller 96 or through external setting port 100 to set the analogue output signal of the amplifier 90 to the full scale range. The offset adjustment 102 input into the converter 86 and the gain adjustment 104 input into the amplifier 90 can also be used to adjust the system (according to the characteristics, and in particular sensitivity, of the sensor 28) into a suitable range for the ADC 92.

The hand-piece 80 also has two depth control buttons 106 that send pulse signals into the micro-controller 96 to set the certain z position for the x-y scan mechanism 20. These buttons 106—one to increase depth, the other to decrease depth—each has a standing voltage of 5 V in the circuit lines 108 to the micro-controller 96. The micro-controller 96 monitors voltage so that when a depth control button 106 is depressed by an operator, the voltage in the respective line 108 drops from 5 V to zero. To allow an operator to control the system, the control buttons 106 are monitored by the micro-controller 96 for either the number of button depressions or the duration of an extended button depression. Each 100 ms of extended depression is treated as equivalent to a single discrete depression. The micro-controller 96 completes the tasks of data collection, data computation and current control. The 12 bit digital signal from ADC 92 and the switch signal from the depth control buttons 106 are sampled in real time, and the micro-controller 96 calculates the values used to control the driver 98 and thence the nitinol wire 28 by means of the proportional integral derivative (PID) control method, where $K_p$ is the proportional coefficient, $K_i$ is the integral coefficient and $K_d$ is the derivative coefficient (see FIG. 4).

Figure 4:
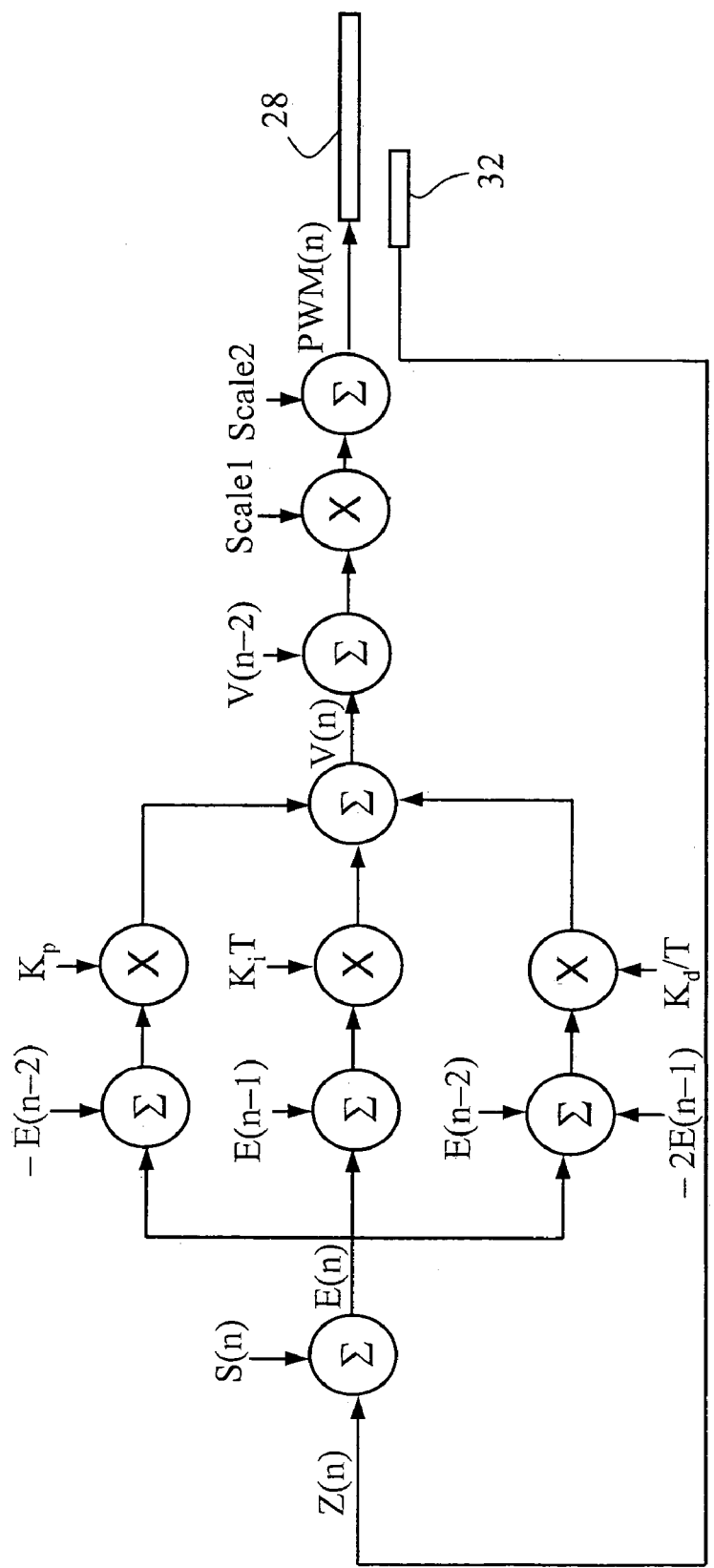
FIG. 4 is a flow chart of the Proportional, Integral and Derivative control loop of the z control apparatus of FIG. 1A.

Referring to the PID control method shown in FIG. 4, Z(n) is the measured position output provided by the position'sensor 32, S(n) the signal from the desired or demand position that is input from the operator by means of the operator buttons 106, E(n) the composite error signal, and T the time control period. V(n) is the intermediate controller output; Scale 1 and Scale 2 rescale V(n). PWM is the Pulse Width Modulation output, which modulates the heating of the wire 28. In this particular implementation of a PID circuit and control method, the error signal from the current iteration E(n) is further modified with error signals from earlier iterations E(n−2) or E(n−1). Similarly the intermediate output of the current iteration V(n) is further modified with V(n−2).

The parameters $K_p$, $K_i$ and $K_d$ are preset and adjustable through the setting port 100, and the current value is output in PWM form. The control period is adjustable in the range 5 ms to 100 ms The system thus forms a closed digital control loop to drive the x-y scan mechanism 20 to a demanded z position or to maintain it at a particular z position, and obtains stable performance by means of the position sensor 32 and the z actuator 26 using the PID control method.

It is possible to set the x-y scan mechanism 20 at a "home" position, for example with a focal plane just outside of the last optical element in the objective optics train 22. Further adjustments are then relative to that home position, and a pair of readouts (not shown) indicate, respectively, the z position relative to the home position and the "absolute" z position, that is, relative to the exterior surface of the forward-most optical element in optics train 22. A home position switch 110 provides the micro-controller a signal to indicate where the home position is. Similarly the "home" position can also function as a "stop" position to prevent the focal plane from moving further rearward than just within the forward-most optical element of objective optics train 22. To meet the varying requirements and characteristics of different position sensors and z actuators (such as in sensitivity), the micro-controller, 96 includes offset adjustment 102 (mentioned above), gain adjustment 104 (mentioned above) and drive current adjustment 112 to allow for adjustment of each component.

The nitinol wire 28 is the key element of the z actuator 26. It is made of the shape-memory alloy nitinol, which contracts in length when heated and stretches to its previous length as it cools down. The small size and good repeatability of nitinol wire make it possible to control the movement of the x-y scan mechanism 20 in the colonoscopy insert 10 with some precision, particularly owing to the use of the position sensor 32 to provide feedback on the position of the x-y scan-mechanism 20. As discussed above, in order to contract and expand the nitinol wire 28, a square wave pulse width modulated current (PWM) is passed through the wire 28. The average value of PWM current will dominate the heating and therefore length of the wire 28. The micro-controller 96 controls the duty cycle of the current pulses to obtain the different average value of PWM current and hence the desired temperature and length. The driver 98 detects from 0 to 5 V and typically converts the PWM voltage to a 0 to 350 mA square wave pulse current form which is transmitted to the nitinol wire 28 to be converted to heat therewithin.

The driver 98 is a voltage to current converter for providing the PWM current to drive the z actuator 26 by selectively heating the wire 28. It operates in switch mode; the current value in "ON" state can be set by a digital potentiometer which is controlled through the setting port 100 or by the micro-controller 96.

FIG. 5A is a schematic representation of the square wave voltage input 114 to the driver 98 following the operator's indication—by suitable control button depression—that he or she wishes to shift the focal plane 38 to be relatively close to the cover slip (not shown) of the colonoscopy insert 10 by shortening the nitinol wire 28. The pulse width 116 is relatively high so that a relatively high average voltage is presented to the driver 98 for a greater average current to be passed through the nitinol wire 28.

Referring to FIG. 5B, when the operator depresses the appropriate depth control button 106, the micro-controller 96 responds to the resultant voltage leak and re-establishes the square wave pattern 118 so that the width 120 of the pulses is smaller and hence a lower average voltage is input to the driver 98. A lower-current is consequently passed-through the nitinol wire 28.

As will be understood, the opposite occurs when the other depth control button 106 is depressed.

In these examples, the effect of the position sensor 32 is to continuously modulate the square wave pattern by feeding the converted digital signal into the micro-controller 96 such that the width 116, 120 of the square wave pulses are constantly varied by small amounts around the required width setting determined by the depth control buttons 106, to correct for undesired variation in the position of the focal plane 38.

Figure 6:
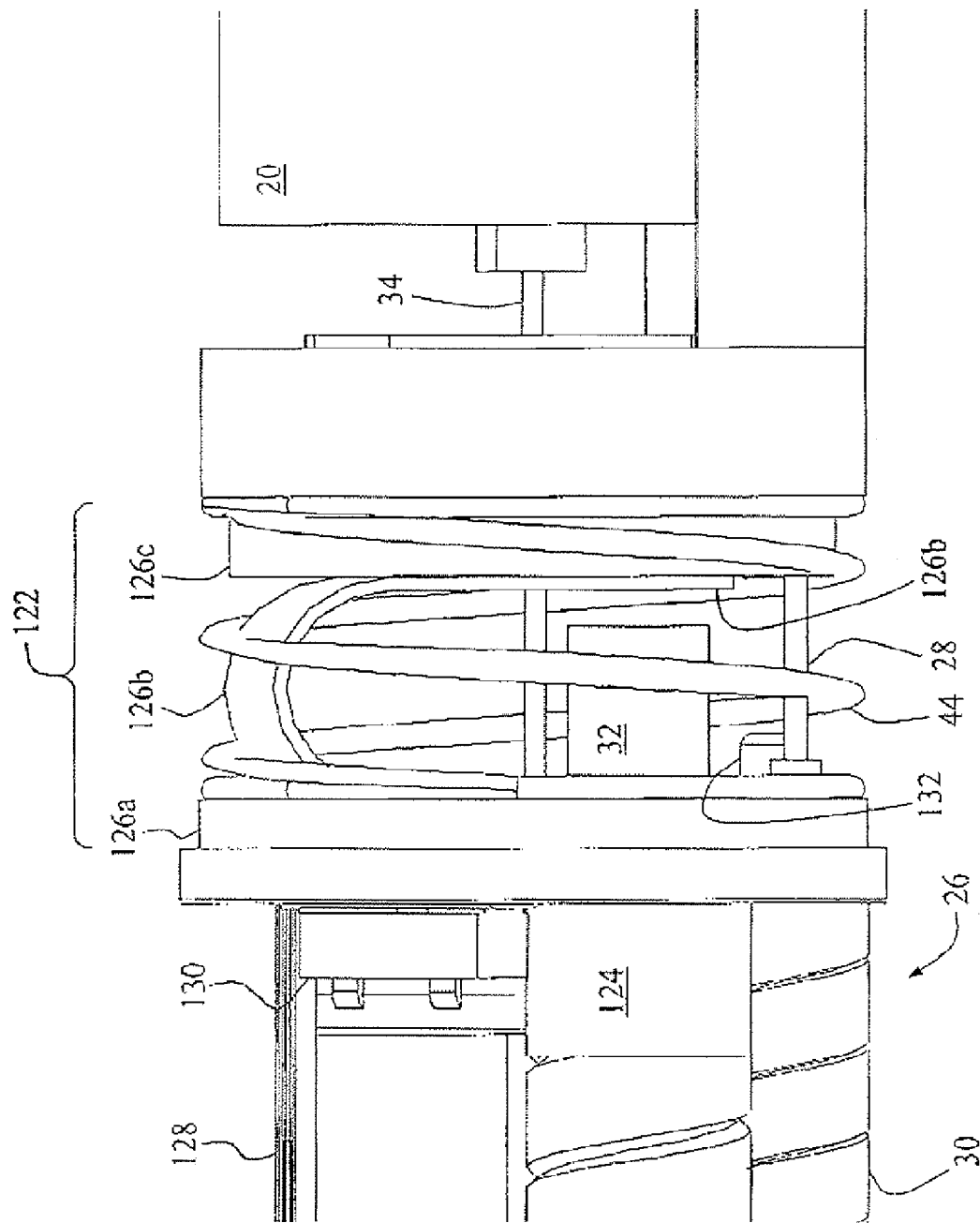
FIG. 6 is a schematic diagram of the arrangement of the spring and optical position sensor with respect to the nitinol wire 28 and x-y scanning mechanism of the z control apparatus of FIG. 1A.

The arrangement of the spring 44 and optical position sensor 32 with respect to the nitinol wire 28 and x-y scanning mechanism 20 is more clearly shown in FIG. 6. As is apparent in this figure, the spring 44 is located in gap 122 (of about 1.3 mm when not in use) forward of the z actuator 26. Both the Bowden Cable 30 (that houses most of the nitinol wire 28) and the rear housing 124 of the position sensor 32 are covered in shrink wrap, which mechanically stabilizes and electrical insulates these components.

Electrical circuitry within the insert 10 is also located on three PCBs 126a, 126b and 126c within gap 122; rear PCB 126a is on the forward end of the z actuator assembly, while forward PCB 126c is on the rear end of the x-y scanning mechanism 20. The size of gap 122 changes during use (as the length of the nitinol wire 28 contracts and expands), so the third or flexible PCB 126b is flexible and arranged in an arc between, and connected to, the other two PCBs. Flexible PCB 126b is firmly secured to the other two PCBs 126a, 126c so that an electrical connection can be maintained across all three PCBs. The use of wire connections, which could break more readily with use and the flexing of soldered connections, is thus avoided.

Also shown in this figure are cabling 128, external circuitry for the x sensor 130 and a back-stop in the form of mechanical pin 132. This last feature provides a rearmost point of travel for the x-y scanning mechanism 20 when the nitinol wire 28 is in its most contracted state. In addition, a current cut-off or monitor may be provided so that the heating-of the nitinol wire 28 is not permitted to increase once the x-y scanning mechanism 20 abuts this mechanical pin 132. Otherwise there is the danger that the nitinol wire 28 would pull itself out of one of its anchor points.

The spring 44 urges against the rear PCB 126a and forward PCB 126c, which rear PCB 126a also provides an attachment surface for the Bowden Cable 30. In addition, optical fiber 34 is enclosed in a sleeve as far forward as the rear of the x-y scanning mechanism 20; this sleeve is preferably sealed against the rear and forward PCBs 126a, 126c to provide some resistance against the admission of dust, microbes and other contaminants.

The nitinol wire 28 is attached at its forward end to forward PCB 126c. As the nitinol wire 28 is repeatedly expanded and contracted during use, the point of attachment to the PCB 126c will be subjected to mechanical stresses that could lead to the loss of that attachment.

Referring to FIG. 7A, according to this embodiment, the nitinol wire 28 is formed into a hook 134 at its forward end and passed through the forward PCB 126c twice. In addition, optional but preferred solder 136 (or alternatively glue) is placed over the end of the hook 134, forming a forward facing cap to hold the nitinol wire 28 in attachment with the PCB 126c.

Referring to FIG. 7B, in an alternatively embodiment the nitinol wire 28 is additionally formed into a knob 138 at its forward end (larger than the hole in the PCB 126c through which the wire 28 passes) so that there is even less likelihood that the hook 134 can become detached from the PCB 126c.

Modifications within the scope of the invention may be readily effected by those skilled in the art. It is to be understood, therefore, that this invention is not limited to the particular embodiments described by way of example hereinabove.

Further, any reference herein to prior art is not intended to imply that that prior art forms or formed a part of the common general knowledge.

We claim:

1. A position control apparatus for controlling position along a depth or z axis, comprising:
    an extensible member that can be extended and contracted along said depth or z axis, comprising shape memory alloy configured and positioned to expand and contract linearly along said depth or z axis;
    a housing for said extensible member and for at least one optical element located forward of said extensible member, said housing constraining said optical element to move linearly along the depth or z axis and limiting buckling of at least a portion of said extensible member when said extensible member is being extended;
    a heater for controlling the temperature of said shape memory alloy; and a feedback mechanism for controlling said heater and responsive to variations in said position;

wherein said position is controllable by said heater and said position can be stabilized by said feedback mechanism; and wherein said extensible member has a forward end coupled to said optical element and a rearward end coupled to said housing at a point rearward of said optical element so that extension and contraction of said extensible member causes said optical element to advance or retreat linearly within said housing along said depth or z axis.

2. An apparatus as claimed in claim 1, further comprising a biaser for opposing either the expansion or contraction of said shape memory alloy.

3. An apparatus as claimed in claim 2, wherein said biaser is opposed to the contraction of said shape memory alloy.

4. An apparatus as claimed in claim 2, wherein said biaser is a spring.

5. An apparatus as claimed in claim 1, wherein said feedback mechanism comprises a feedback sensor for sensing the position of the apparatus and providing an output directed to said heater to modify the heat applied to the shape memory alloy.

6. An apparatus as claimed in claim 1, wherein said feedback mechanism comprises a plurality of feedback sensors.

7. An apparatus as claimed in claim 1, wherein said heater comprises a source of electrical current for heating said shape memory alloy.

8. An apparatus as claimed in claim 7, wherein said source of electrical current is arranged to heat said shape memory alloy by passing said electrical current through said shape memory alloy.

9. An apparatus as claimed in claim 7, wherein said electrical current is a pulse width modulated current.

10. An apparatus as claimed in claim 9, wherein said heater is controllable to vary the duty cycle of the pulse width modulated current and therefore the average value of said electrical current.

11. An apparatus as claimed in claim 1, wherein said feedback mechanism comprises a capacitance sensor, a variable resistance sensor, a magnetic hall sensor, an inductive sensor, or an optical sensor.

12. An apparatus as claimed in claim 1, wherein said feedback mechanism comprises a capacitive sensor comprising a double wire coil capacitive sensor, wherein the separation of the coils of said double wire coil capacitive sensor varies according to the position of said apparatus thereby varying the output of said sensor.

13. An apparatus as claimed in claim 1, wherein said feedback mechanism comprises an optical sensor comprising a pulsed red Light Emitting Diode and a Phase Locked Amplifying detecting diode.

14. An apparatus as claimed in claim 1, wherein said housing comprises an elongate member for housing said portion of said extensible member, said elongate member being longitudinally substantially rigid and laterally flexible.

15. An apparatus as claimed in claim 14, wherein said elongate member comprises a Bowden Cable.

16. An apparatus as claimed in claim 1, wherein said extensible member is one of a plurality of like extensible members.

17. An apparatus as claimed in claim 1, further comprising a flexible printed circuit board arranged between and attached to two portions of said apparatus whose separation varies as the position is varied, to flex as said separation varies.

18. An apparatus as claimed in claim 1, further comprising a home adjustment mechanism for setting a desired home position in the direction of the axis, such that subsequent adjustment of the position is relative to said home position.

19. An endoscope comprising:
an optical fiber for providing illuminating light;
a light condenser for focussing said illuminating light to an observational field; and
a position control apparatus according to claim 1, for controlling the position of the observational field.

20. An endoscope as claimed in claim 19, wherein said position is adjustable by movement of at least an exit aperture of said optical fiber, wherein said movement is controllable by said position control apparatus.

21. An endoscope as claimed in claim 20, wherein said position is adjustable by movement of said exit aperture of said optical fiber and of at least a portion of said light condenser, wherein said movement is controllable by said position control apparatus.

22. An endoscope as claimed in claim 19, wherein said endoscope includes an x-y scan mechanism for x-y scanning light emitted by an exit aperture of said optical fiber, wherein said x-y scan mechanism is configured to x-y scan said light relative to said housing.

23. An endoscope as claimed in claim 22, wherein the position of said x-y scan mechanism relative to said position control apparatus is adjustable by said position control apparatus.

24. An endoscope as claimed in claim 22, wherein said x-y scan mechanism is configured to x-y scan said exit aperture of said optical fiber relative to said housing.

25. An endocsope as claimed in claim 19, wherein said extensible member is one of a plurality of like exstensible members.

26. An endoscope as claimed in claim 19, wherein said endoscope is a confocal endoscope.

27. An endoscope as claimed in claim 19, wherein said endoscope is an endomicroscope.

28. An endoscope as claimed in claim 19, wherein said endoscope includes an x-y scan mechanism within said housing for x-y scanning light emitted by an exit aperture of said optical fiber, wherein said x-y scan mechanism is configured to x-y scan said light relative to said housing.

29. An endoscope as claimed in claim 28, wherein said x-y scan mechanism is coupled to said forward end of said extensible member and the position of said x-y scan mechanism relative to said position control apparatus is adjustable by said position control apparatus.

30. An endoscope as claimed in claim 28, wherein said x-y scan mechanism is configured to x-y scan said exit aperture of said optical fiber relative to said housing.

31. A microscope comprising:
a position control apparatus according to claim 1, for controlling the position of an observational field of said microscope.

32. A colonoscope comprising:
a position control apparatus according to claim 1.

33. A method of providing positioning control of a position along a depth or z axis, comprising:
providing an extensible member that can be extended and contracted along said depth or z axis, comprising shape memory alloy configured and positioned to expand and contract linearly along said depth or z axis;

providing a housing for said extensible member and for at least one optical element located forward of said extensible member, said housing constraining said optical element to move linearly along the depth or z axis and limiting buckling of at least a portion of said extensible member when said extensible member is being extended;

controlling the length of said shape memory alloy by adjusting the temperature of said shape memory alloy;

providing a feedback signal in response to variations in said position and adjusting said temperature according to said feedback signal to stabilize said position; and coupling a forward end of said extensible member to said optical element and a rearward end of said extensible member to said housing at a point rearward of said optical element so that extension and contraction of said extensible member causes said optical element to advance or retreat linearly within said housing along said depth or z axis;

whereby said position is controllable by adjusting said temperature and said position can be stabilized by said feedback signal.

34. A method as claimed in claim 33, further comprising opposing either the expansion or contraction of said shape memory alloy by a biaser.

35. A method as claimed in claim 34, wherein said biaser is a spring.

36. A method as claimed in claim 34, wherein said biaser is opposed to the contraction of said shape memory alloy.

37. A method of performing endoscopy or colonoscopy of a site, comprising:
locating an optical head at said site; and
controlling the position along a depth or z axis of an observational field of said endoscopy or colonoscopy at least in part by a position control apparatus as claimed in claim 1.

38. A method as claimed in claim 37, wherein said endoscope includes an x-y scan mechanism for x-y scanning light emitted by an exit aperture of said optical fiber, and said method includes x-y scanning said light relative to said housing with said x-y scan mechanism.

39. A method as claimed in claim 38, including adjusting the position of said x-y scan mechanism relative to said position control apparatus with said position control apparatus.

40. A method as claimed in claim 38, including x-y scanning said light relative to said housing by x-y scanning said exit aperture of said optical fiber relative to said housing.

41. An endoscope comprising:
an optical fiber for providing illuminating light;
a light condenser for focussing said illuminating light to an observational field; and
a position control apparatus for controlling the position of the observational field, comprising:
an extensible member that can be extended and contracted along a depth or z axis, comprising shape memory alloy configured and positioned to expand and contract linearly along said depth or z axis;
a housing for said extenible member and for at least one optical element located forward of said extensible member, said housing constraining said optical element to move linearly in the depth or z axis;
a heater for controlling the temperature of said shape memory alloy; and
a feedback mechanism for controlling said heater and responsive to variations in said position;
wherein said position is controllable by said heater and said position can be stabilized by said feedback mechanism;
said extensible member has a forward end coupled to said optical element and a rearward end coupled to said housing at a point rearward of said optical element so that extension and contraction of said extensible member causes said optical element to advance or retreat linearly within said housing along said depth or z axis; and
said endoscope includes an x-y scan mechanism for x-y scanning light emitted by an exit aperture of said optical fiber, wherein said x-y scan mechanism is configured to x-y scan said light relative to said housing.

42. An endoscope as claimed in claim 41, wherein the position of said x-y scan mechanism relative to said position control apparatus is adjustable by said position control apparatus.

43. An endoscope as claimed in claim 41, wherein said x-y scan mechanism is configured to x-y scan said exit aperture of said optical fiber relative to said housing.

44. A method of performing endoscopy or colonoscopy of a site comprising:
locating an optical head at said site; and
controlling the position in a depth or z axis of an observational field of said endoscopy or colonoscopy at least in part with a position control apparatus as claimed in claim 41.

* * * * *